(12) United States Patent
Gu

(10) Patent No.: US 12,257,039 B2
(45) Date of Patent: Mar. 25, 2025

(54) HEART RATE DETECTING DEVICE CAPABLE OF ALLEVIATING MOTION INTERFERENCE

(71) Applicant: PixArt Imaging Inc., Hsin-Chu County (TW)

(72) Inventor: Ren-Hau Gu, Hsin-Chu County (TW)

(73) Assignee: PIXART IMAGING INC., Hsin-Chu County (TW)

( * ) Notice: Subject to any disclaimer, the term of this patent is extended or adjusted under 35 U.S.C. 154(b) by 851 days.

(21) Appl. No.: 17/462,622

(22) Filed: Aug. 31, 2021

(65) Prior Publication Data

US 2021/0393156 A1    Dec. 23, 2021

Related U.S. Application Data

(63) Continuation-in-part of application No. 15/460,893, filed on Mar. 16, 2017, now abandoned.

(51) Int. Cl.
*A61B 5/024* (2006.01)
*A61B 5/00* (2006.01)

(52) U.S. Cl.
CPC ...... *A61B 5/02433* (2013.01); *A61B 5/02438* (2013.01); *A61B 5/7271* (2013.01); *A61B 2560/04* (2013.01); *A61B 2562/0238* (2013.01)

(58) Field of Classification Search
CPC ............ A61B 5/02433; A61B 5/02438; A61B 5/7271; A61B 2560/04; A61B 2562/0238; A61B 5/6826; A61B 5/7214; A61B 5/7246; A61B 2562/046; A61B 5/02427
See application file for complete search history.

(56) References Cited

U.S. PATENT DOCUMENTS

| 8,391,943 | B2 * | 3/2013 | Li | A61B 5/14551 600/323 |
| 2008/0033266 | A1 * | 2/2008 | Diab | A61B 5/7246 600/336 |
| 2012/0197137 | A1 * | 8/2012 | Jeanne | A61B 5/0261 600/479 |
| 2018/0160905 | A1 * | 6/2018 | Wang | A61B 5/7246 |
| 2021/0022676 | A1 * | 1/2021 | Lamego | A61B 5/369 |

OTHER PUBLICATIONS

Lee et al. 2020 sensors 20:01493 14 pages (Year: 2020).*
Sidorov et al. 2016 PLoS One 11:e0165413 11pages (Year: 2016).*
Zhang et al. 2021 Optics and Lasers in Engineering 136:106328 8pages (Year: 2020).*

* cited by examiner

*Primary Examiner* — Keith M Raymond
*Assistant Examiner* — Patrick M Mehl
(74) *Attorney, Agent, or Firm* — WPAT, PC

(57) ABSTRACT

This instant disclosure provides a heart rate detecting device which includes an image sensor. The image sensor generates a first mixed signal within a first interval and generates a second mixed signal within a second interval, wherein the first mixed signal contains light information of first multiple light wavelengths having a first intensity ratio from one another, and the second mixed signal contains light information of second multiple light wavelengths having a second intensity ratio, different from the first intensity ratio, from one another.

16 Claims, 8 Drawing Sheets

HEART RATE DETECTING DEVICE CAPABLE OF ALLEVIATING MOTION INTERFERENCE

CROSS REFERENCE TO RELATED APPLICATION

The present application is a continuation-in-part application of U.S. patent application Ser. No. 15/460,893 filed on, Mar. 16, 2017, the disclosure of which is hereby incorporated by reference herein in its entirety.

BACKGROUND OF THE INVENTION

1. Field of the Invention

The instant disclosure relates to a detecting module and method; in particular, to a heart rate detecting module and method.

2. Description of Related Art

Generally, a PPG (photoplethysmogram) system is used to detect the heart rate according to the light brightness (light absorption) using a pulse oximeter which illuminates the skin and measures the changes in light absorption. When the heart contracts that has the maximum peripheral blood volume and light absorption and correspondingly has the minimum light brightness, and when the heart relaxes that has the maximum light brightness. So that a heartbeat can be determined. Accordingly, a heart rate detecting system having a dynamic range capable of detecting the maximum to minimum light intensity is necessary.

In the current PPG system, it usually includes a light source and a detector, and a pixel is used. However, single pixel usually has insufficient dynamic range and may result in high signal-to-noise ratio and so as to decrease the detection accuracy.

Therefore, how to reduce noise influence and upgrade the detection accuracy are important issues in the art.

SUMMARY OF THE INVENTION

In order to overcome the abovementioned problem, the instant disclosure provides a heart rate detecting module which includes an image sensor and a processor. Via the image sensor including a CMOS (complementary metal oxide silicon) sensor array to generate displacement information of light intensity gravity centers and the processor calculating a light intensity variance, a broad dynamic range can be obtained.

To achieve the abovementioned purpose, one of the embodiments of the instant disclosure provides a heart rate detecting device which includes a first light source, a second light source and an image sensor. The first light source is configured to emit a first wavelength light. The second light source is configured to emit a second wavelength light. The image sensor is configured to generate a first mixed signal within a first interval and generate a second mixed signal within a second interval. The first wavelength light and the second wavelength light have a first intensity ratio within the first interval, and have a second intensity ratio, different from the first intensity ratio, within the second interval.

Another embodiment of the instant disclosure provides a heart rate detecting device which includes an image sensor. The image sensor is configured to generate a first mixed signal within a first interval and generate a second mixed signal within a second interval, wherein the first mixed signal contains light information of first multiple light wavelengths having a first intensity ratio from one another, and the second mixed signal contains light information of second multiple light wavelengths having a second intensity ratio, different from the first intensity ratio, from one another.

Another embodiment of the instant disclosure provides a heart rate detecting device which includes an image sensor. The image sensor is configured to generate a first mixed signal within a first interval and generate a second mixed signal within a second interval, wherein the first mixed signal contains light information of a first light combination of multiple light wavelengths, and the second mixed signal contains light information of a second light combination of multiple light wavelengths, wherein the second light combination includes at least one light wavelength not included in the first light combination.

Another embodiment of the instant disclosure provides a heart rate detecting device which includes an image sensor and a processor. The image sensor is configured to generate a plurality of image frames according to a first light combination of multiple light wavelengths or a second light combination of multiple light wavelengths from a subject. The processor is configured to output a heart rate value based on a light intensity variance of the plurality of image frames associated with the first light combination or the second light combination.

In order to further appreciate the characteristics and technical contents of the instant disclosure, references are hereunder made to the detailed descriptions and appended drawings in connection with the instant disclosure. However, the appended drawings are merely shown for exemplary purposes, rather than being used to restrict the scope of the instant disclosure.

DETAILED DESCRIPTION OF THE PREFERRED EMBODIMENTS

Embodiments of heart rate detecting module and method disclosed in the instant disclosure are illustrated via specific examples as follows, and people familiar in the art may easily understand the advantages and efficacies of the instant disclosure by disclosure of the specification. The instant disclosure may be implemented or applied by other different specific examples, and each of the details in the specification may be applied based on different views and may be modified and changed under the existence of the spirit of the instant disclosure. The figures in the instant disclosure are only for brief description, but they are not depicted according to actual size and do not reflect the actual size of the relevant structure. The following embodiments further illustrate related technologies of the instant disclosure in detail, but the scope of the instant disclosure is not limited herein.

[First Embodiment]

Figure 1:
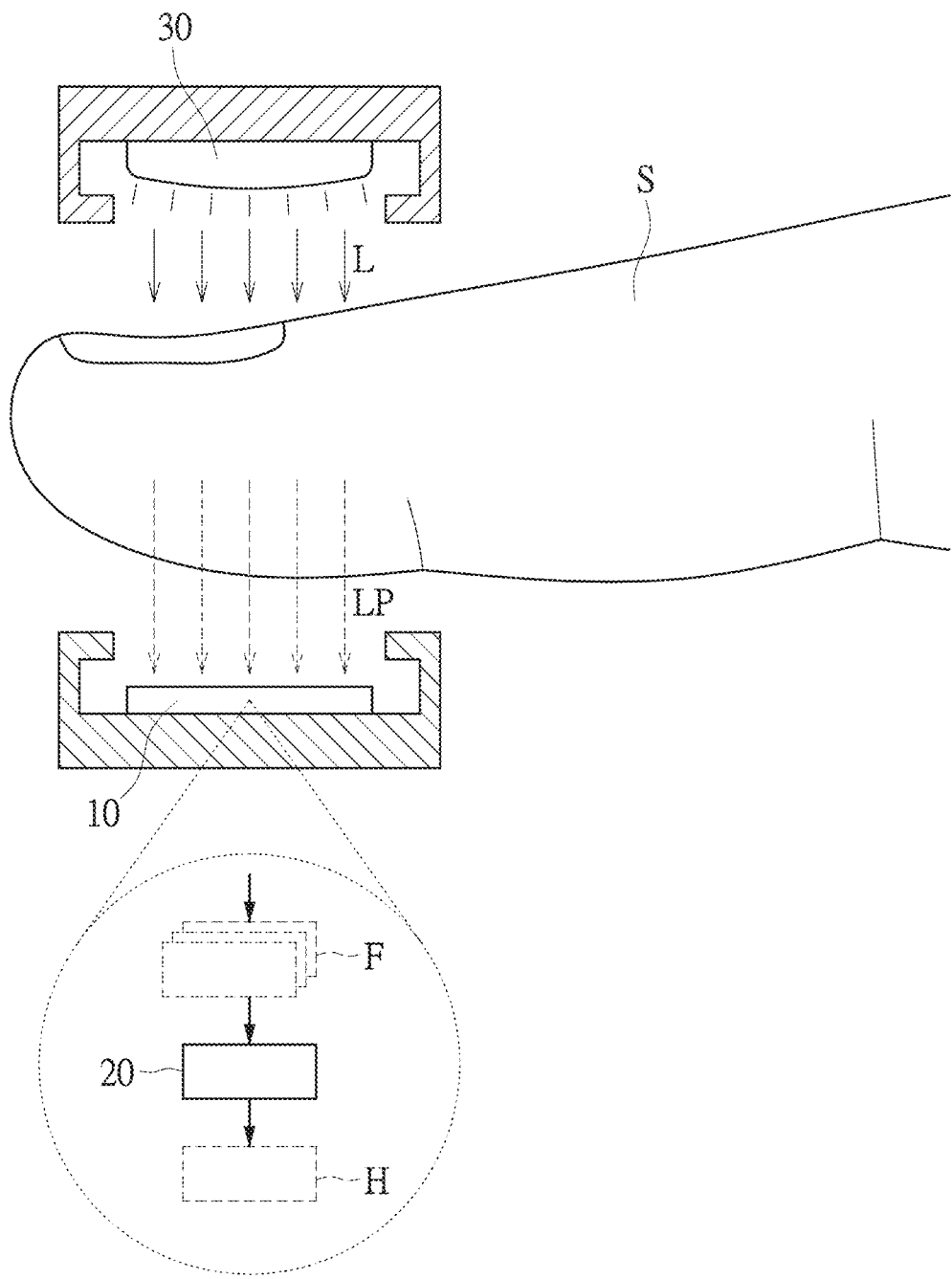
FIG. 1 is a schematic view of a heart rate detecting module of an embodiment about light passing through a subject in the instant disclosure.
Figure 2:
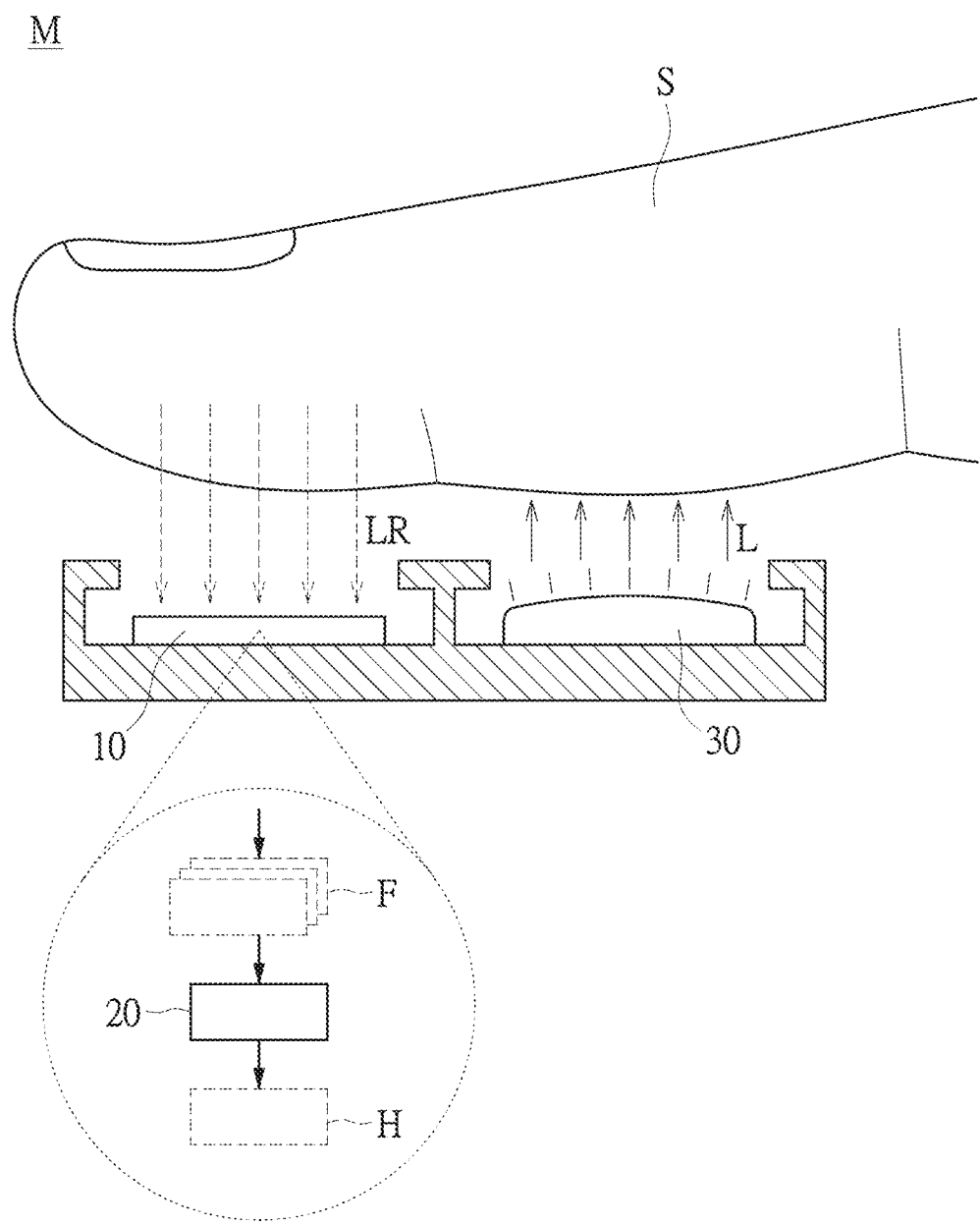
FIG. 2 is a schematic view of a heart rate detecting module of an embodiment about light being reflected from a subject in the instant disclosure.
Figure 4:
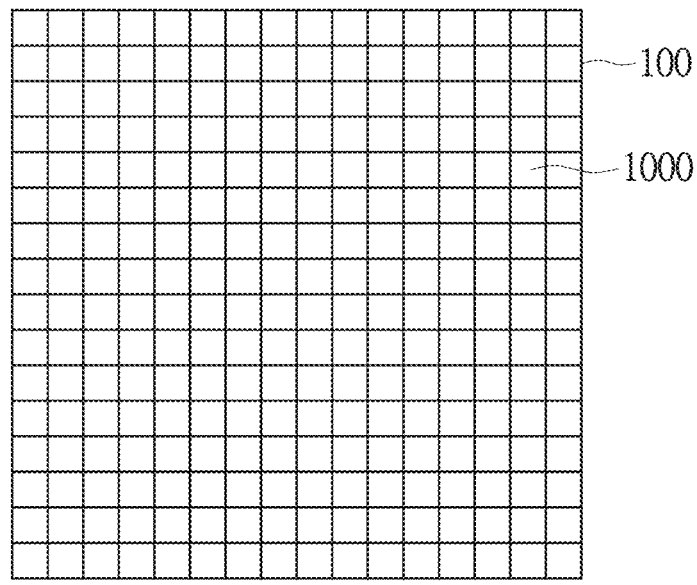
FIG. 4 is a schematic view of an image sensor of an embodiment in the instant disclosure.

Please refer to FIG. 1, FIG. 2 and FIG. 4. FIG. 1 shows a schematic view of a heart rate detecting module of the first embodiment about light passing through a subject in the instant disclosure, FIG. 2 shows a schematic view of a heart rate detecting module of the first embodiment about light being reflected from a subject in the instant disclosure, and FIG. 4 shows a schematic view of an image sensor of the first embodiment in the instant disclosure. As shown in FIG. 1, the heart rate detecting module M of this embodiment includes an image sensor 10, a processor 20 and a light source 30. However, in other embodiments, the heart rate detecting module M may include a plurality of image sensors 10, processors 20 and light sources 30, and the number of the image sensors 10, the processors 20 and the light sources 30 can be selected depending on requirements. In more details of FIG. 1, the image sensor 10 includes a sensor array which contains a plurality of pixels and is used to generate a corresponding plurality of image frames F. In this embodiment, the sensor array is a complementary metal oxide silicon (CMOS) sensor array 100. The CMOS sensor array 100 includes a plurality of pixels 1000 (as shown in FIG. 4), and the plurality of pixels 1000 of the CMOS sensor array 100 receives the light passing through the subject S (referred to passed light LP hereinafter) to generate an image frame F. In this embodiment, the processor 20 is a digital signal processor (DSP), and is used to output a heart rate value H. The light source 30 may be light-emitting diodes or laser lights, and is used to emit a light L toward to a subject S. The light L may have a limited bandwidth to improve the CMOS sensor array 100 sensing the light L. Furthermore, the processor 20 controls the light source 30, so that the light source 30 can keep lighting on or intermittently lighting on. For example, the processor 20 controls the light source 30 to emit the light L for 20 times per second; in one embodiment, the CMOS sensor array 100 of the image sensor 10 samples in a rate (i.e. sample rate) synchronizing to a flash rate of the light source 30 and therefore receives the passed light LP for 20 times and generates 20 image frames F. In the embodiment of FIG. 1, the CMOS sensor array 100 of the image sensor 10 samples in the rate synchronizing to the flash rate of the light source 30 to improve a sensing result, but the present disclosure is not limited thereto. In other embodiments, the CMOS sensor array 100 of the image sensor 10 samples in the rate non-synchronizing to the flash rate of the light source 30.

As shown in FIG. 2, the image sensor 10 includes a sensor array which contains a plurality of pixels and is used to generate a plurality of image frames F as described in the embodiment in FIG. 1. In this embodiment, the sensor array is a CMOS sensor array 100 which includes a plurality of pixels 1000 (as shown in FIG. 4), and the plurality of pixels 1000 of the CMOS sensor array 100 receives the light reflected from the subject S (referred to reflected light LR hereinafter) to generate an image frame F. The plurality of pixels 1000 of the CMOS sensor outputs intensity values to generate an image and generates a plurality of image frames F depending on a sample rate of the image sensor 10.

In this embodiment, the processor 20 is a DSP, and is used to output a heart rate value H. The light source 30 may be light-emitting diodes or laser lights, and is used to emit a light L toward to a subject S. Furthermore, the processor 20 controls the light source 30, so that the light source 30 can keep lighting on or intermittently lighting on. In the embodiment of FIG. 2, The CMOS sensor array 100 of the image sensor 10 samples in a rate (i.e. sample rate) synchronizing to the flash rate of the light source 30 and therefore receives the reflected light LR and generates image frames F.

Figure 3:
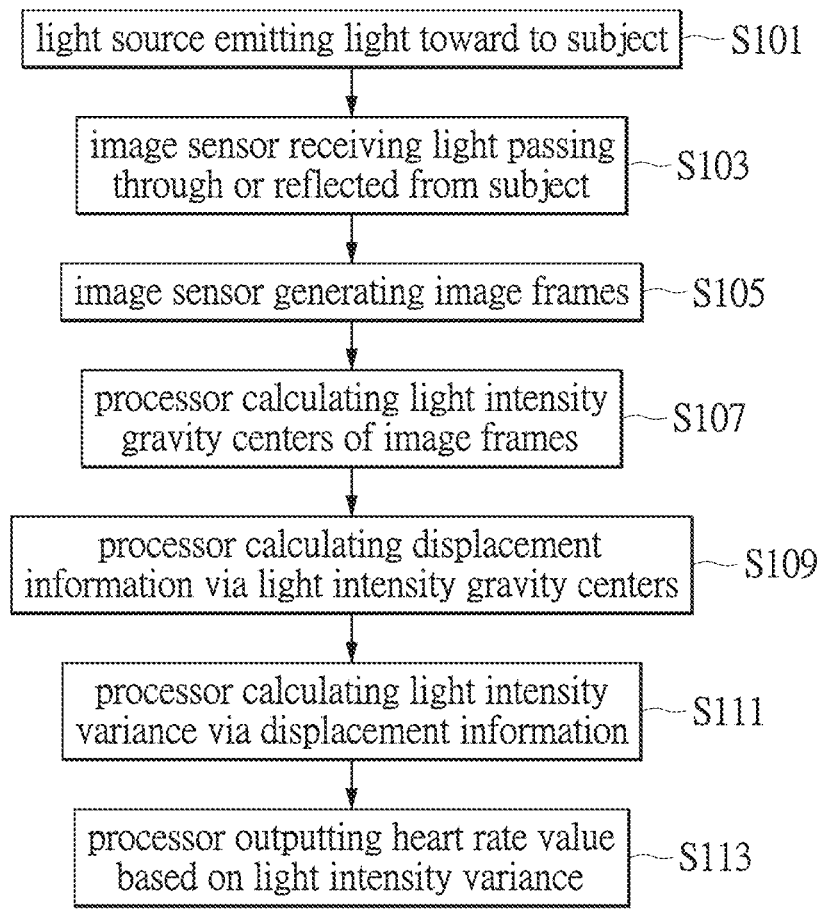
FIG. 3 is a flowchart of a heart rate detecting method of an embodiment in the instant disclosure.
Figure 5:
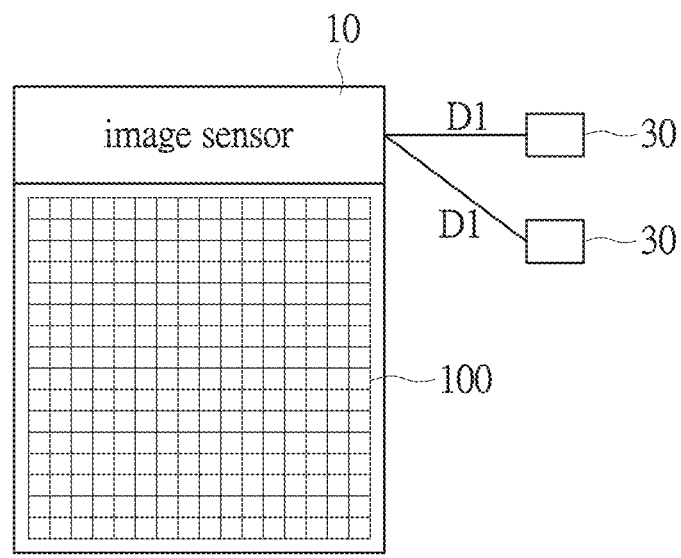
FIG. 5 is a schematic view of a placement of an image sensor and a light source.

The instant disclosure focuses on calculating the heart rate according to a depth displacement (referred to displacement information hereinafter) of a surface (skin) being measured. The change of the depth from the surface to the CMOS sensor array 100 will cause a change of the light intensity gravity center of the passed light LP or the reflected light LR. Therefore, the displacement information can be calculated via a change of the light intensity gravity centers of the passed light LP or the reflected light LR, and a method for calculating the change of the light intensity gravity centers is described below. Specifically, please refer to steps S101 to S113 in FIG. 3 and FIG. 5. FIG. 3 shows a flowchart of a heart rate detecting method of the first embodiment in the instant disclosure, and FIG. 5 shows a schematic view of a placement of an image sensor 10 and a light source 30. Firstly, as shown in FIG. 3 and FIG. 5, in the steps S101 and S103, the processor 20 controls the light source 30 to emit the light L toward to the subject S, the image sensor 10 is disposed at a distance D1 from the light source 30, in one embodiment the distance D1 is within a distance range selected from 1.8 mm to 4 mm, from 2.8 mm to 4 mm or from 3.8 mm to 4 mm. In FIG. 5, the distance D1 is illustrated as 4 mm. In the next step S105, the image sensor 10 generates a plurality of image frames F according to the passed light LP or the reflected light LR. Then, in the steps S107 to S113, the processor 20 calculates positions of the light intensity gravity centers of at least two of the plurality of image frames F generated from the image sensor 10 (in step S107). According to the difference of two positions of the light intensity gravity centers, the displacement information of the light intensity gravity centers is calculated by the processor 20 (in step S109), and a light intensity variance is then calculated by the processor 20 (in step S111) via the displacement information. In addition, the displacement information contains an X displacement data, a Y displacement data and a photoplethysmography data. The displacement information is a difference between two positions of the light intensity gravity center at different times. Where the position of the light intensity gravity center can be determined by a coordinate of each pixel and corresponding intensity values, such as list in formula (I) as follows.

$$\Sigma(Pi \times Ii)/\Sigma Ii = PGC \quad (I)$$

In the formula (I), Pi represents a corresponding coordinate of each of the plurality of pixels 1000, and contains the coordinate of X, and the coordinate of Y. The PGC can be determined by two-dimensional coordinate system (containing X and Y coordinates) but also can be determined by one-dimensional coordinate system (containing only X or Y coordinate), wherein the two one-dimensional PGC (X coordinate and Y coordinate) can be combined as the two-dimensional PGC. Ii represents an intensity of the passed light LP or the reflected light LR received by each of the plurality of pixels 1000. ΣIi represents a sum of intensities of the passed light LP or the reflected light LR received by the plurality of pixels 1000. PGC (position of gravity center) represents the light intensity gravity center of each captured image, wherein displacement information is a difference value of two positions of gravity centers of two frames. Finally, the processor 20 outputs the heart rate value H based on the displacement information of the light intensity gravity centers of the plurality of image frames F. In addition, there are various methods for calculating the light intensity gravity centers in prior arts, and the aforementioned formula listed herein is only one of them. However, the method for calculating the light intensity gravity centers is not limited herein.

Figure 6A:
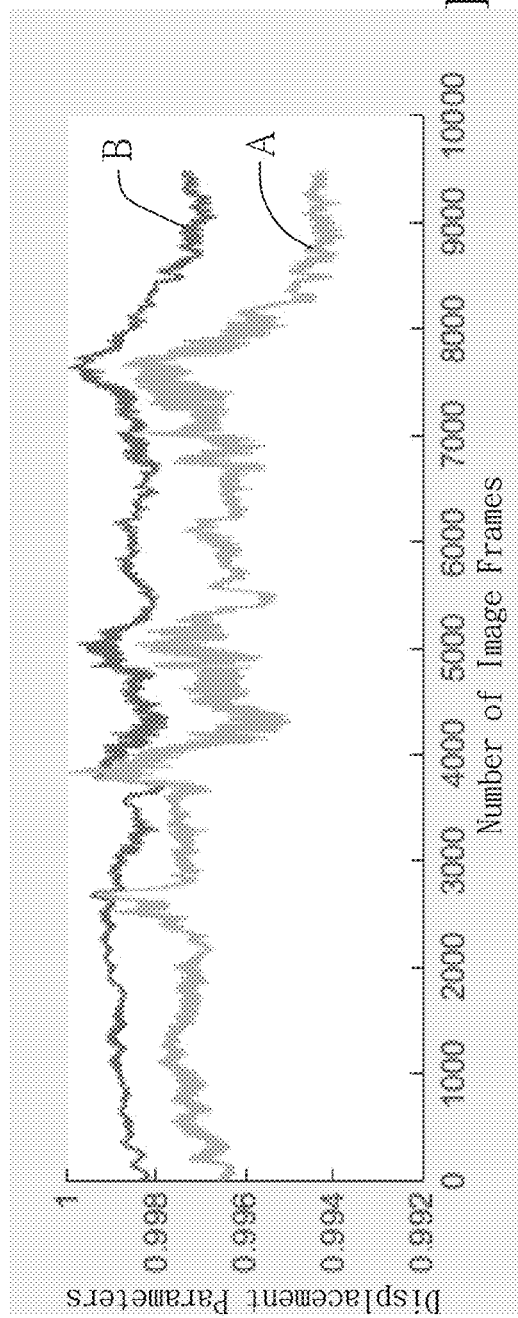
FIGS. 6A and 6B are heart rate detecting results measured by the heart rate detecting module of the instant disclosure.
Figure 6B:
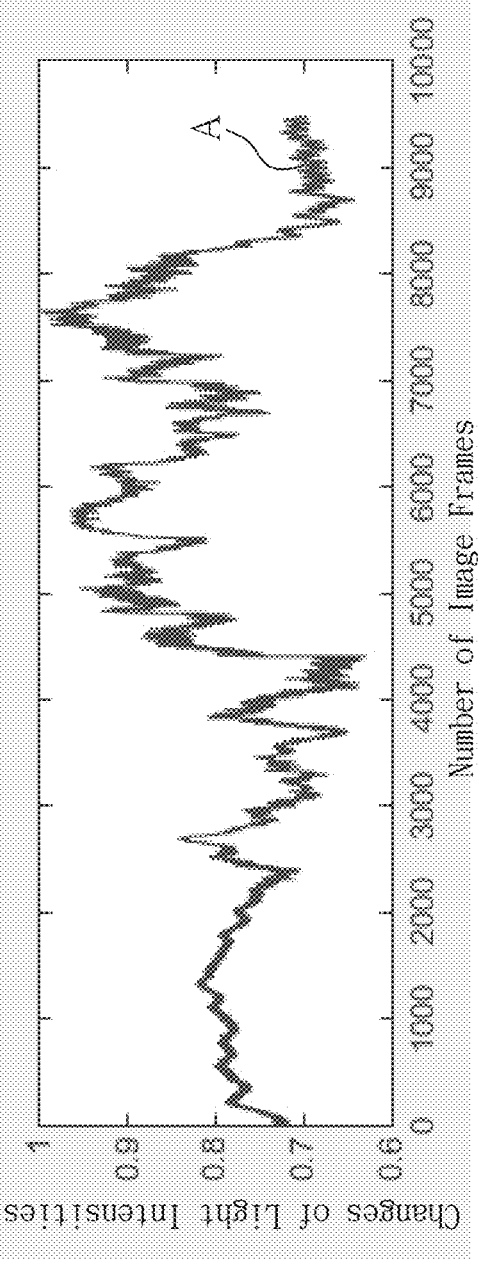

Please refer to FIGS. 6A and 6B. FIGS. 6A and 6B show heart rate detecting results of a motion activation measured by the heart rate detecting module M of the instant disclosure. In other words, the results of the heart rate detecting module M of the instant disclosure are shown in FIG. 6A and FIG. 6B. In FIG. 6A, the horizontal axis represents a number of image frames F, for example the number 1000 means the 1000-th frame captured by the image sensor 10, which is obtained from a runner's heart rates during running on a treadmill over time. In FIG. 6A, from number 0 to about number 2200, the runner was resting and started to run with a speed of 5 km/hr lasting for 1 minute (from number 2200 to about number 3600). As shown from number 3600 to number 5500, the speed was increased to 9 km/hr lasting for 1 minute. Then, from number 5500 to number 6500, the speed was slowed down to 3 km/hr lasting for 1 minute. Next, the speed was increased to 7 km/hr lasting for 1 minute from number 6500 to number 7800, and after that the runner was resting (from number 7800). The longitudinal axis represents displacement parameters that are the pulse beating causing height changes of the detected skin, wherein the value from 0 to 1 represents the level of the height changes of the detected skin (value 0 represents no displacement and value 1 represents maximum displacement). Specifically, when the heart is beating, the blood would be outputted to generate vibrations, so as to make displacements of the skin called displacement parameters. There are a displacement of X direction (the lower line: A line) and a displacement of Y direction (the upper line: B line) have been shown in FIG. 6A. In which, the maximum of the displacement parameter is 1, and there is the maximum displacement parameter at number 7800.

As shown in FIG. 6B, the conditions of heart rate detection is identical to aforementioned FIG. 6A, and thus it is not repeated herein. The horizontal axis represents the number of image frames F, and the longitudinal axis represents changes of light intensity, wherein the value from 0 to 1 represents the level of the intensity changes of the captured image frame (value 0 represents no change and value 1 represents maximum change). Specifically, when the heart is beating, the blood would be outputted to generate vibrations, so as to make the changes of light intensity of the skin. There is only a PPG (photoplethysmogram) (A line) been shown in FIG. 6B. In FIG. 6B, the maximum of the changes of light intensity is 1, and there is the maximum change of light intensity at number 7800.

According to above, it is shown that, the heart rate detecting module M of the instant disclosure can measure the X displacement, the Y displacement and the PPG, and the results can be compensated to decrease disturbing signals of motion (such as hands waving during running) and improve detection accuracy.

Since the heart rate detecting module M of this instant disclosure not only can generate the PPG data but also can generate the X displacement data and the Y displacement data, such that it can reduce interferences to output highly accurate heart rate results.

Accordingly, if a detecting module only can output a PPG data like a traditional detecting module in prior arts, only one piece of pixel is used to receive the light. Thus, the dynamic range is insufficient, and the change of the PPG is limited, such that the noise of the heart rate detection signal is hard to be reduced.

Comparing to the prior arts, since the heart rate detecting module M of the instant disclosure has the CMOS sensor array 100 which is composed of a plurality of pixels 1000, each of the pixels 1000 receive the reflected light LR or the passed light LP and the results obtained therefrom can be summed up, thus a broad dynamic range can be obtained. Furthermore, the displacement information has two-dimensional information which contains an X displacement data, a Y displacement data, such that the noise of the heart rate detection signal (e.g., motion signal) can be effectively reduced to increase the accuracy of the heart rate result.

[Second Embodiment]

A heart rate detecting module M of the second embodiment in the instant disclosure includes an image sensor 10 and a processor 20. The image sensor 10 generates a plurality of laser speckles according to a laser light from a subject S. The processor 20 outputs a heart rate value H based on a change of at least one displacements of the plurality of laser speckles.

Figure 7:
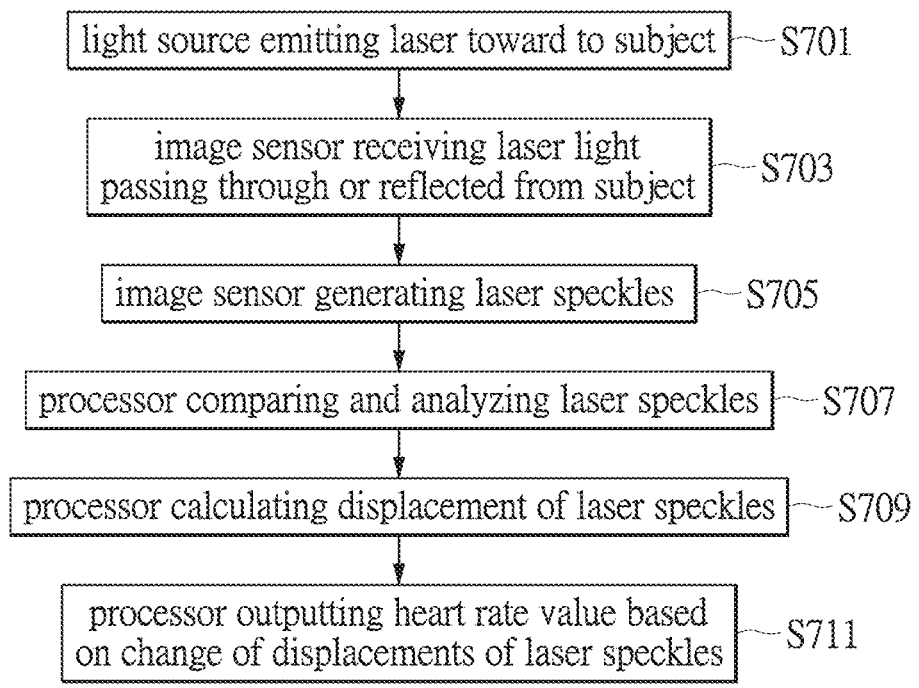
FIG. 7 is a flowchart of a heart rate detecting method of the second embodiment in the instant disclosure.

Please refer to FIG. 7. FIG. 7 shows a flowchart of a heart rate detecting method of the second embodiment in the instant disclosure. The heart rate detecting method of the second embodiment is a speckle pixel positioning method. Specifically, it includes the following steps, as shown in steps S701 to S711 in FIG. 7, a heart rate detecting method of the second embodiment in the instant disclosure includes the following steps. Firstly, in step S701 and step S703, a light source 30 is used to emit a laser light toward to a subject S, then an image sensor 10 receives the laser light passing through or reflected from the subject S (passed light LP and reflected light LR respectively). Next, in step S705, a plurality of laser speckles is generated according to the laser light from the subject S by an image sensor 10. Then, in step S707 and step S709, a processor 20 is used to compare and analyze the plurality of laser speckles, and to calculate changes of the plurality of laser speckles, that is at least one displacements of the plurality of laser speckles are calculated by the processor 20. Finally, the processor 20 outputs a heart rate value H based on a change or changes of the at least one displacements of the plurality of laser speckles.

In the second embodiment of the instant disclosure, except to the aforementioned heart rate detecting module M and the detecting method thereof, other technical features obtained therefrom are identical to those of the first embodiment in the instant disclosure, and thus are not repeated herein.

[Third Embodiment]

Figure 8:
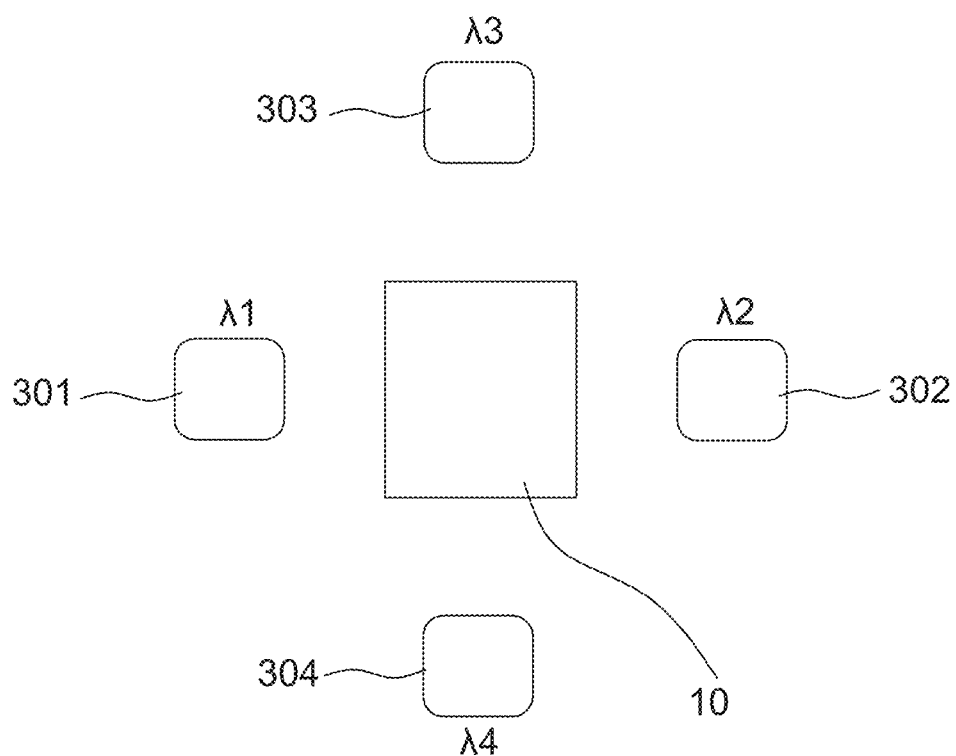
FIG. 8 is an arrangement of an image sensor and multiple light sources of different wavelengths.

Please refer to FIG. 8, it is a schematic diagram of the arrangement of the image sensor 10 and multiple light sources (e.g., four light sources 301-304 shown herein) of a heart rate detecting device, which includes the heart rate detecting module M mentioned above, of the present disclosure. Details of the image sensor 10 have been described above, and thus are not repeated herein. The heart rate detecting device could be integrated on a portable electronic device or a wearable electronic device or accessory.

A first light source 301 emits light of a first wavelength λ1. A second light source 302 emits light of a second wavelength λ2. A third light source 303 emits light of a third wavelength λ3. A fourth light source 304 emits light of a fourth wavelength λ4. In the present disclosure, λ1, λ2, λ3 and λ4 are not totally identical.

Figure 9:
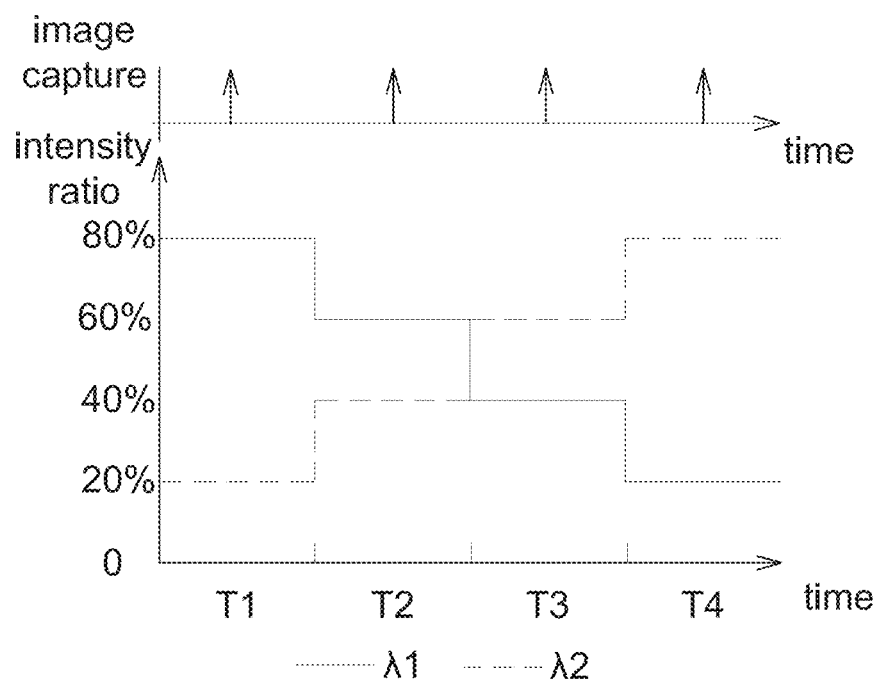
FIG. 9 is an operational diagram of a heart rate detecting device according to a third embodiment of the present disclosure.

Please refer to FIG. 9, it is an operational diagram of a heart rate detecting device according to a third embodiment of the present disclosure. It is assumed that a summation of intensity of multiple light sources illuminating on a subject (e.g., user's skin) has an intensity sum. FIG. 9 shows a ratio of light intensity of the first wavelength λ1 with respect to the intensity sum as well as a ratio of light intensity of the second wavelength λ2 with respect to the intensity sum within different intervals T1 to T4.

Referring to FIGS. 8 and 9 together, an example using two light sources, e.g., 301 and 302, is illustrated hereinafter.

In one aspect, first wavelength light emitted by the first light source 301 is green light and second wavelength light emitted by the second light source 302 is red light, or vice versa. In another aspect, the first wavelength light is green light and the second wavelength light is infrared light, or vice versa. Various combinations of light may be selected.

The first light source 301 and the second light source 302 emit light of different intensity (i.e. having different driving currents) corresponding to different intervals, e.g., shown as T1, T2, T3 and T4 in FIG. 9. Each interval is, for example, about 5 to 20 seconds, but not limited thereto. The image sensor 10 samples at a sample rate for the whole or a part of intervals T1 to T4.

The image sensor 10 generates a first mixed signal within a first interval T1 and generates a second mixed signal within a second interval T2. In the third embodiment, signals generated by the image sensor 10 are called mixed signal because in each interval, the first light source 301 and the second light source 302 emit light together (i.e. intensity sum) such that the passed light or reflected light contain information associated with both λ1 and λ2. As mentioned above, the mixed signal is generated according to a plurality of image frames F generated by the image sensor 10.

For example, FIG. 9 shows that the first wavelength light and the second wavelength light have a first intensity ratio (e.g., λ1/λ2=4) within the first interval T1; have a second intensity ratio (e.g., λ1/λ2=1.5), different from the first intensity ratio, within the second interval T2; have a third intensity ratio (e.g., λ1/λ2=2/3) within the third interval T3; and have a fourth intensity ratio (e.g., λ1/λ2=1/4) within the fourth interval T4. That is, in different intervals, the first wavelength light is stronger or weaker than the second wavelength light.

As mentioned above, the processor 20 (e.g., DSP, ASIC or MCU) controls the first light source 301 and the second light source 302 to change emission intensity within the first interval T1 and second interval T2, e.g., as shown in FIG. 9.

The processor 20 then decorrelates or decouples the first mixed signal and the second mixed signal (using both the first and second mixed signals) to obtain a first decorrelated signal and a second decorrelated signal. The decorrelation method includes, for example, independent component analysis (ICA), blind source separation (BSS) or the like, but not limited there to. It is known that The ICA and BSS methods are mainly used to separate combined signals. Therefore, one of the first decorrelated signal and the second decorrelated signal is assumed as a motion signal (i.e. the noise mentioned herein) and the other one is assumed as a non-motion signal, which is used to calculate a heart rate value herein. That is, the non-motion signal is the motion-free PPG signal.

In one aspect, the processor 20 recognizes or distinguishes the non-motion signal by comparing the first decorrelated signal and the second decorrelated signal with historical signals generated by the image sensor 10.

For example, when there is no motion, magnitudes of the first decorrelated signal and the second decorrelated signal have a significant difference, e.g., larger than a threshold. When the processor 20 identifies that a magnitude difference (in time domain or frequency domain) is larger than or equal to the threshold, the processor 20 records (e.g., in the memory) the signal distribution (i.e. magnitudes in time axis) of one of the first decorrelated signal and the second decorrelated signal having a larger magnitude as a reference signal. That is, the one of the first decorrelated signal and the second decorrelated signal having a larger magnitude is considered as PPG signal. It is appreciated that the processor 20 converts the first decorrelated signal and the second decorrelated signal into frequency if necessary.

Then, in the scenario that the magnitude difference during operation becomes smaller than the threshold, the processor 20 compares the first decorrelated signal and the second decorrelated signal with the recorded reference signal, and identifies one of the first decorrelated signal and the second decorrelated signal having higher similarity (in time domain or frequency domain) with the recorded reference signal as the non-motion signal.

In another aspect, the processor 20 recognizes or distinguishes the non-motion signal, among the first decorrelated signal and the second decorrelated signal, by comparing (in time domain or frequency domain) the first decorrelated signal and the second decorrelated signal with a G-sensor signal, performed simultaneously with acquiring the first mixed signal and the second mixed signal. That is, the heart rate detecting device of the present disclosure further includes a G-sensor (e.g., a MEMS device) performing the detection corresponding to different intervals, e.g., T1 to T4 shown in FIG. 9, to generate the G-sensor signal corresponding to the first mixed signal and the second mixed signal. The processor 20 recognizes one of the first decorrelated signal and the second decorrelated signal having higher similarity with the G-sensor signal as the motion signal, and the other one of the first decorrelated signal and the second decorrelated signal having lower similarity with the G-sensor signal as the non-motion signal.

As mentioned above, a number of light sources emitting light within every interval T1 to T4 as shown in FIG. 9 are not limited to two. For example, the first mixed signal generated by the image sensor 10 contains light information of a first light combination of multiple (at least two) light wavelengths, and the second mixed signal generated by the image sensor 10 contains light information of a second light combination of multiple (at least two) light wavelengths. In one aspect, the second light combination includes at least one light wavelength not included in the first light combination.

In one aspect, if one light wavelength, among the multiple light wavelengths, is included in both of the first light combination and the second light combination, said one light wavelength has different intensity in the first interval and the second interval.

The third embodiment is combinable with the above first and second embodiments. For example, in FIGS. 6A and 6B, 0 to 2200 frames are captured corresponding to interval T1 as shown in FIG. 9 by using a first combination of light intensity of wavelengths λ1 and λ2; 2200 to 3600 frames are captured corresponding to interval T2 as shown in FIG. 9 by using a second combination of light intensity of wavelengths λ1 and λ2; 3600 to 5500 frames are captured corresponding to interval T3 as shown in FIG. 9 by using a third combination of light intensity of wavelengths λ1 and λ2; 5500 to 6500 frames are captured corresponding to interval T4 as shown in FIG. 9 by using a fourth combination of light intensity of wavelengths λ1 and λ2; and so on.

In the third embodiment, the signal generated by the image sensor 10 (e.g., A and B shown in FIGS. 6A and 6B) is not directly used as the displacement information or PPG mentioned in the above first and second embodiments. The signal generated by the image sensor 10 is firstly decorrelated to obtain a non-motion signal (i.e., removing motion component), and then the non-motion signal is used as the displacement information or PPG mentioned above for calculating the heart rate value. For example, signals A and B shown in FIGS. 6A and 6B are mixed signals, and the decorrelation performed by the processor 120 removes the motion component from the mixed signals.

For example referring to FIG. 3 again. In the Step S101, multiple light sources, e.g., a first light combination of multiple light wavelengths or a second light combination of multiple light wavelengths, emit light toward a subject. In the Step S103, the image sensor 10 receives a combination of light (i.e. intensity sum) passing through or reflected from the subject. In the Step S105, the image sensor 10 generates a plurality of image frames according to the first light combination of multiple light wavelengths or the second light combination of multiple light wavelengths from the subject. Then, a heart rate value based on a light intensity variance of the plurality of image frames associated with the first light combination or the second light combination. For example, the processor 20 uses image frames associated with the first light combination to sequentially perform the Steps S107 to S113 to calculate heart rate value based on light intensity variance; or, the processor 20 uses image frames associated with the second light combination to sequentially perform the Steps S107 to S113 to calculate heart rate value based on light intensity variance. Details of the Steps S107 to S113 have been illustrated above, and thus are not repeated.

In one aspect, the first light combination includes at least one light wavelength different from the second light combination. In another aspect, the first light combination is totally different from the second light combination. In another aspect, the first light combination is the same as the second light combination.

In one aspect, an intensity ratio between the multiple light wavelengths in the first light combination is different (partially or totally) from that in the second light combination.

In an alternative aspect, the processor 20 outputs the heart rate value based on the light intensity variance associated with the first light combination and the second light combination, alternatively. For example, in the intervals T1 and T3 of FIG. 9, the first light combination is used to illuminate the subject, and in the intervals T2 and T4 of FIG. 9, the second light combination is used to illuminate the subject.

It is appreciated that the mixed signal generated by the image sensor 10 is not limited to contain light information of only two wavelengths. The mixed signal contains light information of more wavelengths if more light sources are used.

Figure 10:
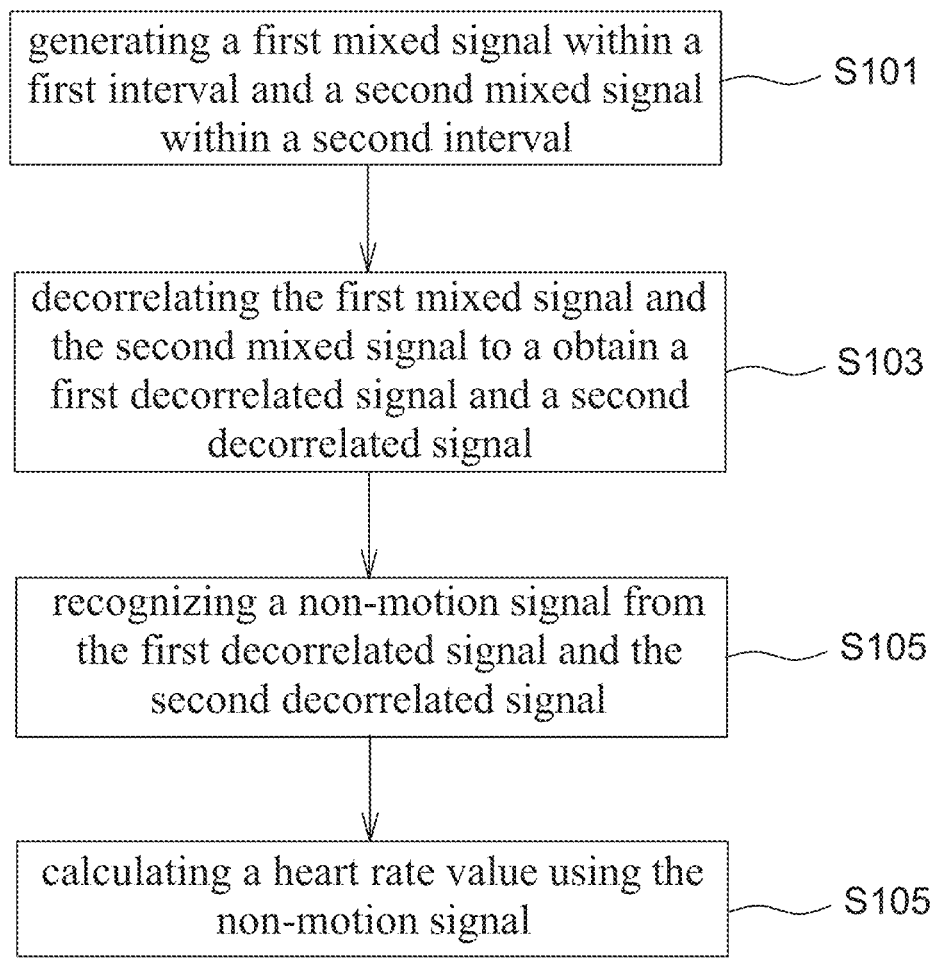
FIG. 10 is a flow chart of an operating method of a heart rate detecting device according to a third embodiment of the present disclosure.

Please refer to FIG. 10, it is a flow chart of an operating method of a heart rate detecting device according to a third embodiment of the present disclosure, including the steps of: generating a first mixed signal within a first interval and generating a second mixed signal within a second interval (Step S101); decorrelating the first mixed signal and the second mixed signal to a obtain a first decorrelated signal and a second decorrelated signal (Step S103); recognizing a non-motion signal from the first decorrelated signal and the second decorrelated signal (Step S105); and calculating a heart rate value using the not-motion signal (Step S107).

Step S101: The first mixed signal contains light information of first multiple light wavelengths having a first intensity ratio from one another, and the second mixed signal contains light information of second multiple light wavelengths having a second intensity ratio, different from the first intensity ratio, from one another.

In one aspect, the first multiple light wavelengths are totally different from the second multiple light wavelengths. For example as shown in FIG. 8, λ1, λ2, λ3 and λ4 are different from one another. For example, in the first interval T1, the first light source 301 and the second light source 302 illuminate the subject; but in the second interval T2, the third light source 303 and the fourth light source 304 illuminate the subject. Light intensity of different wavelengths λ1, λ2, λ3 and λ4 are totally different or partial different in each time interval, e.g., T1 to T4 shown in FIG. 9. The processor 20 decorrelates mixed signals obtained within T1 and T2.

In another aspect, the first multiple light wavelengths are partially different from the second multiple light wavelengths. For example, in three intervals T1 to T3 of FIG. 9, λ1 is used in all the three intervals. However, in the interval T1, λ1 and λ2 illuminate the subject; in the interval T2, λ1 and λ3 illuminate the subject; and in the interval T3, λ1 and λ4 illuminate the subject, but the present disclosure is not limited thereto. The processor 20 decorrelates mixed signals obtained within T1, T2 and T3.

In an alternative aspect, in the interval T1, λ1 and λ2 illuminate the subject; in the interval T2, λ2 and λ3 illuminate the subject; and in the interval T3, λ3 and λ4 illuminate the subject, but the present disclosure is not limited thereto. The processor 20 decorrelates mixed signals obtained within T1, T2 and T3.

In another aspect, the first multiple light wavelengths are totally identical to the second multiple light wavelengths, e.g., FIG. 9 showing two light sources 301 and 302 emitting light at different intensity in every interval.

Step S103: The processor 20 uses decorrelation method, e.g., including ICA and BSS, to separate the combined signal, i.e. PPG signal and motion signal herein, to obtain decorrelated signals.

Step S105: As mentioned above, the processor 20 compares the decorrelated signals (e.g., including decorrelated first signal and the decorrelated second signal) with the historical signals generated by the image sensor 10 to recognize or distinguish the non-motion signal; or compares the decorrelated signals with a G-sensor signal to recognize or distinguish the non-motion signal.

Step S107: After obtaining the non-motion signal, the processor 20 uses the method mentioned in the above first and second embodiments to calculate a heart rate value.

It is appreciated that a number of intervals for generating mixed signals to be decorrelated by the processor 20 is not limited to 4 as shown in FIG. 9. It is appreciated that a number of light sources for emitting light within each interval is not particular limited, e.g., using two, three or four light sources.

Because different light will receive different influences from the motion, using different intensity combinations within different intervals can help the decorrelation process performed by the processor 20 to accurately separate motion signal and non-motion.

In summary, this instant disclosure has the benefit that, via the heart rate detecting module including the CMOS sensor array of the image sensor which can generate the displacement information of light intensity gravity centers and the displacements of laser speckles, and the processor calculating the light intensity variance and changes of the displacements of the laser speckles, a broad dynamic range can be obtained. Therefore, the noise of detection signal can be reduced and the detection accuracy can be upgraded.

The descriptions illustrated supra set forth simply the preferred embodiments of the instant disclosure; however, the characteristics of the instant disclosure are by no means restricted thereto. All changes, alterations, or modifications conveniently considered by those skilled in the art are deemed to be encompassed within the scope of the instant disclosure delineated by the following claims.

What is claimed is:

1. A heart rate detecting device, comprising:
   a first light source, configured to emit a first wavelength light;
   a second light source, configured to emit a second wavelength light; and
   an image sensor configured to generate a first mixed signal within a first interval upon the first light source and the second light source emitting light together and generate a second mixed signal within a second interval upon the first light source and the second light source emitting light together,
   wherein the first wavelength light and the second wavelength light have a first intensity ratio within the first interval, and have a second intensity ratio, different from the first intensity ratio, within the second interval, and
   decorrelation of the first mixed signal and the second mixed signal is configured to calculate a heart rate value.

2. The heart rate detecting device as claimed in claim 1, further comprising a processor configured to control the first light source and the second light source to change emission intensity within the first interval and second interval.

3. The heart rate detecting device as claimed in claim 2, wherein the processor is further configured to
   decorrelate the first mixed signal and the second mixed signal to a obtain a first decorrelated signal and a second decorrelated signal, and
   recognize a non-motion signal from the first decorrelated signal and the second decorrelated signal to calculate the heart rate value.

4. The heart rate detecting device as claimed in claim 3, wherein the processor is configured to recognize the non-motion signal by comparing the first decorrelated signal and the second decorrelated signal with historical signals generated by the image sensor.

5. The heart rate detecting device as claimed in claim 3, wherein the processor is configured to recognize the non-motion signal by comparing the first decorrelated signal and the second decorrelated signal with a G-sensor signal.

6. The heart rate detecting device as claimed in claim 1, wherein
   the first wavelength light is green light and the second wavelength light is red light, or
   the first wavelength light is green light and the second wavelength light is infrared light.

7. The heart rate detecting device as claimed in claim 1, wherein
   within the first interval, the first wavelength light is stronger than the second wavelength light, and
   within the second interval, the first wavelength light is weaker than the second wavelength light.

8. A heart rate detecting device, comprising:
   an image sensor configured to generate a first mixed signal within a first interval and generate a second mixed signal within a second interval, wherein the first mixed signal contains light information of first multiple light wavelengths emitting together and having a first intensity ratio from one another, and the second mixed signal contains light information of second multiple light wavelengths emitting together and having a second intensity ratio, different from the first intensity ratio, from one another,
   wherein decorrelation of the first mixed signal and the second mixed signal is configured to calculate a heart rate value.

9. The heart rate detecting device as claimed in claim 8, wherein the first multiple light wavelengths are totally different from the second multiple light wavelengths.

10. The heart rate detecting device as claimed in claim 8, wherein the first multiple light wavelengths are partially different from the second multiple light wavelengths.

11. The heart rate detecting device as claimed in claim 8, wherein the first multiple light wavelengths are totally identical to the second multiple light wavelengths.

12. The heart rate detecting device as claimed in claim 8, further comprising a processor configured to
   decorrelate the first mixed signal and the second mixed signal to a obtain a first decorrelated signal and a second decorrelated signal, and
   recognize a non-motion signal from the first decorrelated signal and the second decorrelated signal to calculate the heart rate value.

13. The heart rate detecting device as claimed in claim 12, wherein the processor is configured to recognize the non-motion signal by comparing the first decorrelated signal and the second decorrelated signal with historical signals generated by the image sensor.

14. The heart rate detecting device as claimed in claim 12, wherein the processor is configured to recognize the non-motion signal by comparing the first decorrelated signal and the second decorrelated signal with a G-sensor signal.

15. A heart rate detecting device, comprising:
   an image sensor configured to generate a first mixed signal within a first interval and generate a second mixed signal within a second interval, wherein the first mixed signal contains light information of a first light combination of multiple light wavelengths emitting together, and the second mixed signal contains light information of a second light combination of multiple light wavelengths emitting together, wherein the second light combination includes at least one light wavelength not included in the first light combination,
   wherein decorrelation of the first mixed signal and the second mixed signal is configured to calculate a heart rate value.

16. The heart rate detecting device as claimed in claim 15, wherein one light wavelength included in both the first light combination and the second light combination has different intensity in the first interval and the second interval.

* * * * *